United States Patent
Grebius et al.

(10) Patent No.: US 9,968,392 B2
(45) Date of Patent: May 15, 2018

(54) METHOD AND ASSEMBLY FOR PREPARING AND DISPENSING A PASTE

(71) Applicant: PROMIXA MEDICAL AB, Lund (SE)

(72) Inventors: Staffan Grebius, Lund (SE); Sten Drennow, Lund (SE); Ulf Larsson, Malmö (SE)

(73) Assignee: PROMIXA MEDICAL AB, Lund (SE)

( * ) Notice: Subject to any disclaimer, the term of this patent is extended or adjusted under 35 U.S.C. 154(b) by 258 days.

(21) Appl. No.: 14/777,197

(22) PCT Filed: Mar. 14, 2014

(86) PCT No.: PCT/EP2014/055152
§ 371 (c)(1),
(2) Date: Sep. 15, 2015

(87) PCT Pub. No.: WO2014/140304
PCT Pub. Date: Sep. 18, 2014

(65) Prior Publication Data
US 2016/0038209 A1   Feb. 11, 2016

Related U.S. Application Data

(60) Provisional application No. 61/800,655, filed on Mar. 15, 2013.

(30) Foreign Application Priority Data

Mar. 15, 2013 (SE) ...................... 1300197

(51) Int. Cl.
*A61B 17/88* (2006.01)
*B01F 11/00* (2006.01)
(Continued)

(52) U.S. Cl.
CPC ...... *A61B 17/8833* (2013.01); *A61B 17/8822* (2013.01); *B01F 11/0054* (2013.01);
(Continued)

(58) Field of Classification Search
CPC .. A61B 17/88; A61B 17/8822; A61B 17/8833
See application file for complete search history.

(56) References Cited

U.S. PATENT DOCUMENTS 6,796,701 B2   9/2004   Wahlig et al.
7,513,679 B2   4/2009   Grebius
(Continued)

FOREIGN PATENT DOCUMENTS

EP   1 259 200 B1   8/2005
EP   1 685 812 A2   8/2006
(Continued)

OTHER PUBLICATIONS

International Search Report for International Application No. PCT/EP2014/055152, dated Jul. 10, 2014.
(Continued)

*Primary Examiner* — Christopher Beccia
(74) *Attorney, Agent, or Firm* — Merchant & Gould P.C.

(57) ABSTRACT

An assembly for preparing and dispensing a paste, preferably bone cement, includes a cylinder containing a powder and a receptacle containing a liquid. A piercing device is configured to open the receptacle to allow liquid to flow into the cylinder to be mixed with the powder. The receptacle is collapsed by a differential pressure between the cylinder and the receptacle.

32 Claims, 11 Drawing Sheets

(51) Int. Cl.
  *B01F 13/00* (2006.01)
  *B01F 15/00* (2006.01)
  *B01F 15/02* (2006.01)
(52) U.S. Cl.
  CPC .... *B01F 13/0023* (2013.01); *B01F 15/00506* (2013.01); *B01F 15/0212* (2013.01); *B01F 15/0225* (2013.01); *B01F 15/0256* (2013.01); *B01F 15/0258* (2013.01); *B01F 15/0279* (2013.01); *A61B 2017/8838* (2013.01); *B01F 2215/0029* (2013.01)

(56) References Cited

U.S. PATENT DOCUMENTS

2003/0021180 A1* 1/2003 Wahlig ............... A61B 17/8827
   366/139
2004/0196735 A1* 10/2004 Barker ............... A61B 17/8833
   366/139
2005/0128867 A1* 6/2005 Henniges ........... A61B 17/8822
   366/139
2006/0226043 A1* 10/2006 Smith ..................... A61J 1/067
   206/438

FOREIGN PATENT DOCUMENTS

EP          1 741 413 A1    1/2007
WO    WO 2010/002346 A1    1/2010

OTHER PUBLICATIONS

Written Opinion for International Application No. PCT/EP2014/055152, dated Jul. 10, 2014.

* cited by examiner

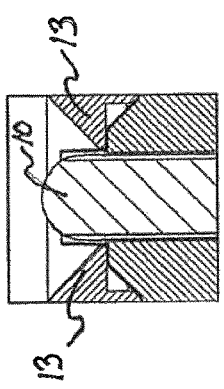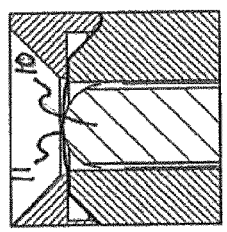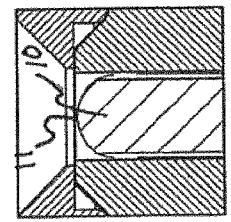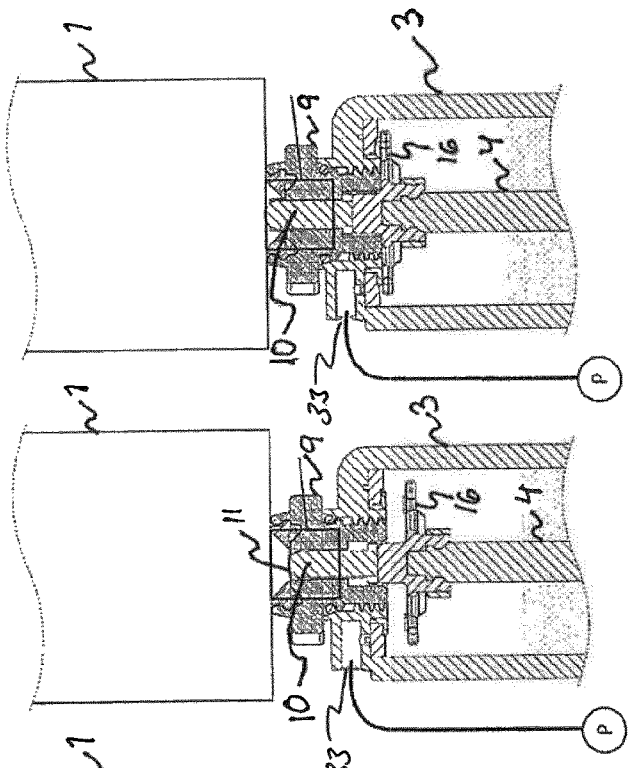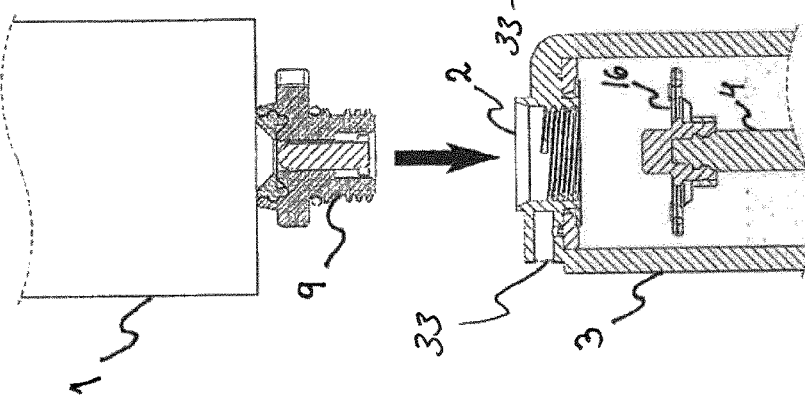

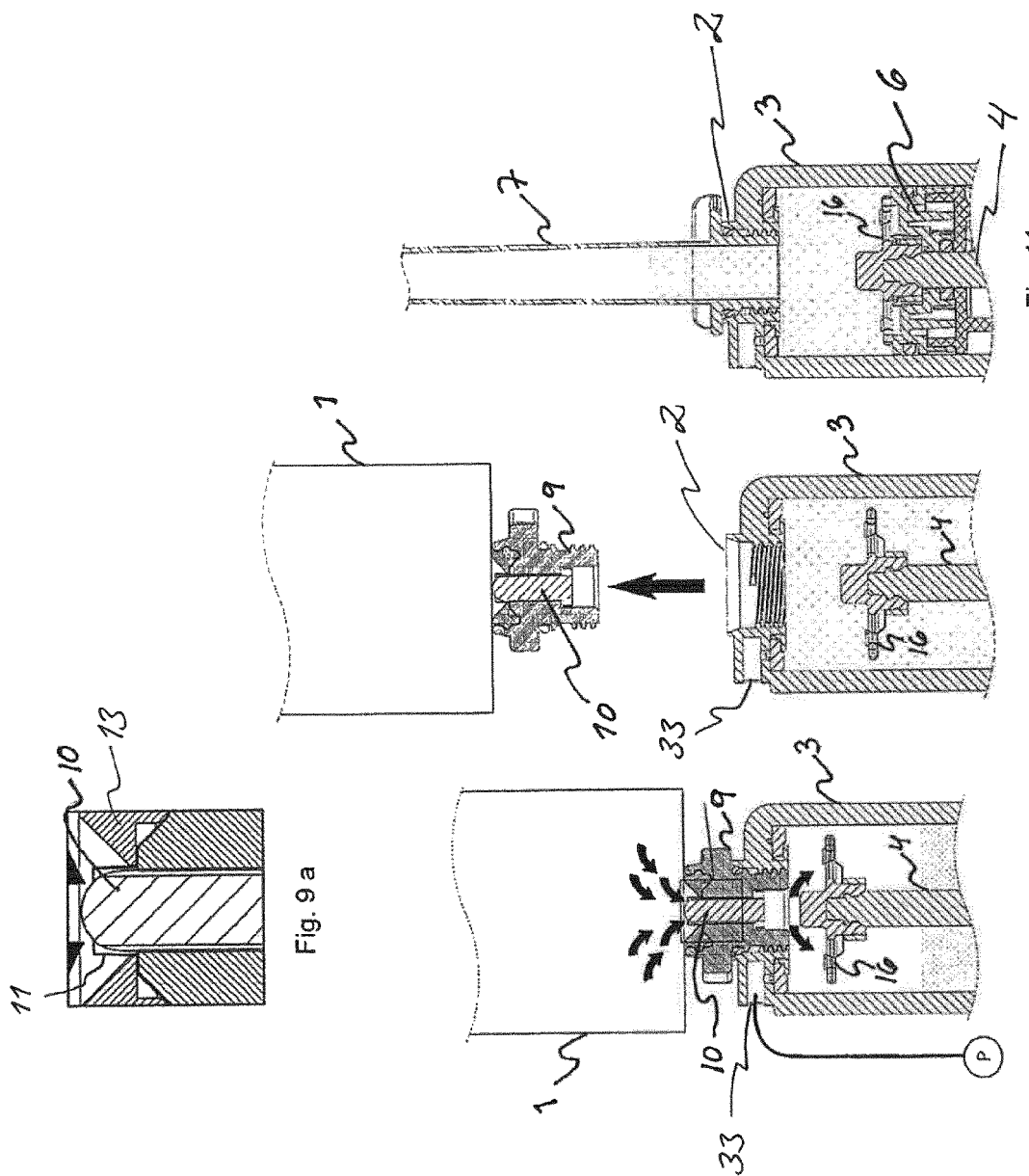

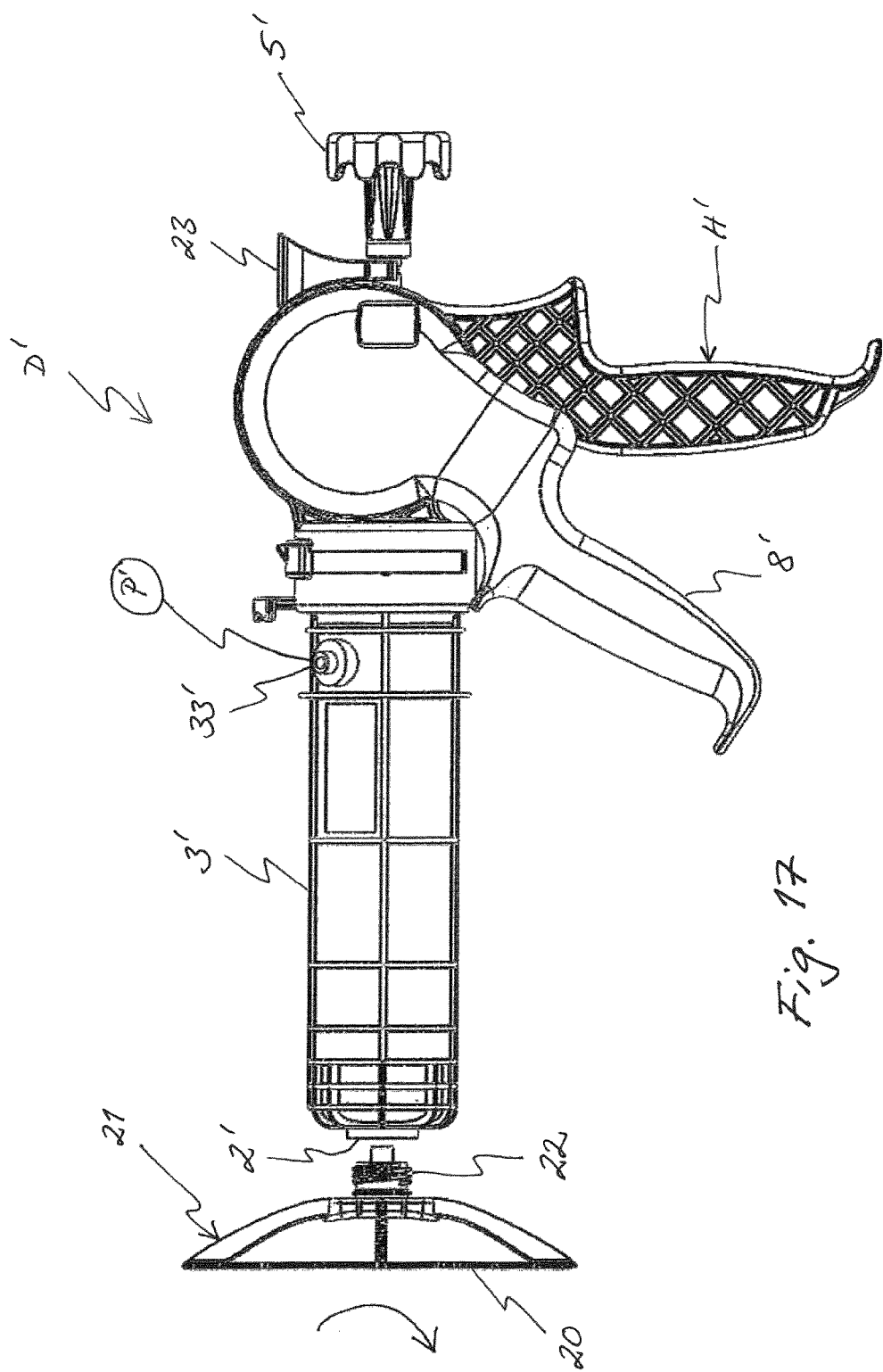

METHOD AND ASSEMBLY FOR PREPARING AND DISPENSING A PASTE

This application is a National Stage Application of PCT/EP2014/055152, filed 14 Mar. 2014, which claims benefit of Serial No. 1300197-9, filed 15 Mar. 2013 in Sweden and Ser. No. 61/800,655, filed 15 Mar. 2013 which applications are incorporated herein by reference. To the extent appropriate, a claim of priority is made to each of the above disclosed applications.

TECHNICAL FIELD

The present invention relates to a method and an assembly for bringing a powder and a liquid component in contact with each other for mixing to a paste, such as bone cement, and for dispensing the paste to a surgical area.

BACKGROUND

Handling of bone cement in such surgery as replacement of hip joints is a crucial step. The mixing of bone cement components, a powder and a liquid (monomer), has to occur no more than about 30 seconds prior to application of the mixed bone cement, and the device used for mixing therefore needs to be simple and quick to handle.

WO-A-2010/002346 discloses a bone cement mixing device which has a piston displaceable in a cylinder, and a piston rod with a mixing member for mixing and subsequent dispension of the bone cement to the surgical area. Before use, a funnel is attached to the cylinder through which funnel the powder and the liquid are fed into the cylinder. During this filling, the device is placed vertically on a base member with the funnel upwards. In a following step, the funnel and the base member are removed and the free end of the cylinder is closed, prior to mixing. After mixing of the bone cement components, a dispensing tube is connected to the free end of the cylinder and used for applying the bone cement to the operative area, e. g. a joint. This mixing and dispensing device has been tested in practice with good results. However, there is still room for improvements. The filling, mixing and dispensing of bone cement involve several steps of adding components as well as connecting and removing parts to the cylinder. Although performed within the time limit of 30 seconds, these steps are time-consuming and somewhat stressful for the user.

Another type of bone cement mixer/dispenser is known from EP-A-1,741,413 where the powder is contained inside a mixing container and the liquid is kept in liquid containers extending alongside the mixing container. The liquid containers are then opened by means of a cannula through which the liquid flows into the mixing container to be mixed with the powder by a piston rod. This method of delivering the liquid to the container requires additional equipment in the form of two brackets alongside the mixing container which hold the liquid containers. A drawback of this mixer/dispenser and similar solutions is that the brackets take up a large proportion of the external portion of the mixing container which makes this prior-art device bulky and difficult to operate. Also, the opening of the liquid containers sideways by cannulas requires an unnecessary complex structure. For instance, if only one liquid container is to be emptied, the structure involves the addition of a cap at the cannula not to be used. The cap prevents the sealing means of the cannula from loosening during handling.

A further example of a bone cement dispensing device is disclosed in U.S. Pat. No. 6,796,701 which basically suffers from the same drawbacks as discussed above.

From the above, it is evident that there is room for improvements of prior-art mixing and dispensing devices of this kind.

SUMMARY

Accordingly, the present invention seeks to mitigate, alleviate or eliminate one or more of the above-identified deficiencies in the art and disadvantages singly or in any combination and solves at least the above mentioned problems by providing a novel assembly and a novel method. Hence, the aim of the invention is to facilitate the handling of a mixing and dispensing device, and to improve it also in other ways.

These objects have now been achieved by the technique set forth in the appended independent claims; certain embodiments being defined in the dependent claims.

Since the liquid-containing collapsible receptacle is connected to the same connection end portion which is used for connection of the dispensing tube, a very efficient mixing and dispensing assembly is achieved. This favourable connection also makes it possible to use the mixing means within the cylinder to activate the moveable opening/piercing device which can be provided either on the receptacle or the cylinder.

The design of the inventive assembly is compact and easy to handle by users. The opening/piercing device breaks a wall of the receptacle in an efficient manner and the liquid is smoothly fed into the cylinder by the differential pressure between the receptacle and the cylinder. Preferably, this differential pressure is achieved by a vacuum source connected to the cylinder but other alternatives are available. For instance, the flexible receptacle can be subject to an external pressure which forces the liquid into the cylinder to be mixed with the powder contained therein.

The flexible liquid receptacle is preferably accommodated in a cavity of a dome-shaped base unit which—after connection to the powder cylinder—can be placed on a table when the mixing step is to be performed. This promotes efficient mixing.

BRIEF DESCRIPTION OF THE DRAWINGS

In the following, embodiments of the invention will be described in more detail, reference being had to the accompanying schematic drawings which illustrate non-limiting examples of how the invention can be reduced into practice and in which:

FIG. 5 shows the connection of a liquid-containing receptacle to a cylinder.

FIGS. 6-8 show piercing of a receptacle by a piercing element according to an embodiment of the invention; FIGS. 6a, 7a, 8a illustrating details on a larger scale, FIG. 9 shows how liquid is fed into the cylinder after the receptacle has been pierced, FIG. 10 shows release of the receptacle from a connecting portion of the cylinder, FIG. 11 shows a dispensing tube connected to the connecting portion of the cylinder, FIG. 17 is a side view of a mixing/dispensing assembly according to a further embodiment of the invention, in preparation mode.

DETAILED DESCRIPTION OF EMBODIMENTS

The present invention concerns an assembly and a method suitable for mixing a powder and a liquid component into a paste, such as bone cement, to be used in a surgical procedure. The basic components of the pre-loaded mixing gun assembly may be of the type known from WO-A-2010/002346 which is incorporated herein by reference. The mixing gun is preferably of single-use type.

FIGS. 1-4 give an overview of how a mixing/dispensing assembly in accordance with a first embodiment is prepared for use in a series of steps. A dispenser D has a handle section H and a cylinder section C to be further described below.

Figure 1:
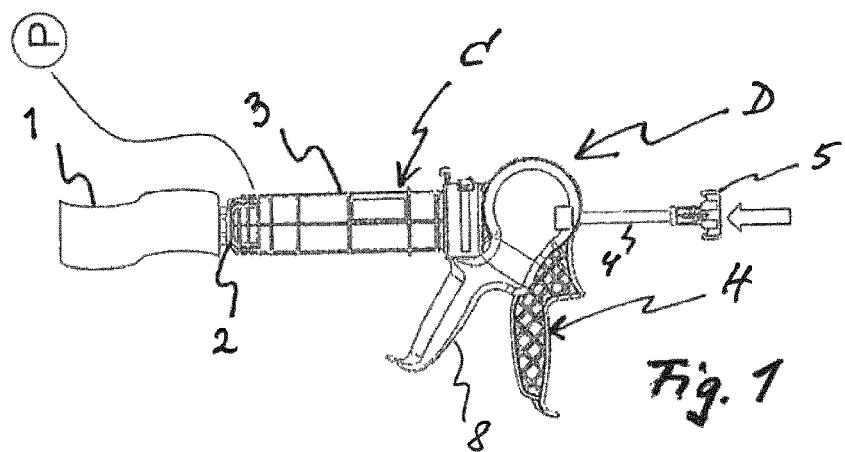
FIGS. 1-4 are side views of an assembly according to an embodiment of the invention in different operation modes.

In a first step shown in FIG. 1 a receptacle 1 containing a liquid component of the paste is connected via a connecting portion 2 to a cylinder 3 containing a powder component of the paste. Preferably, the liquid is a monomer and the powder is a kind of bone cement powder. The receptacle 1 is pierced in a manner to be described, said piercing opening up the receptacle 1 and allowing the liquid component to flow in to the powder component within the cylinder 3. Preferably, the receptacle 1 is made of a flexible plastics material.

Figure 2:
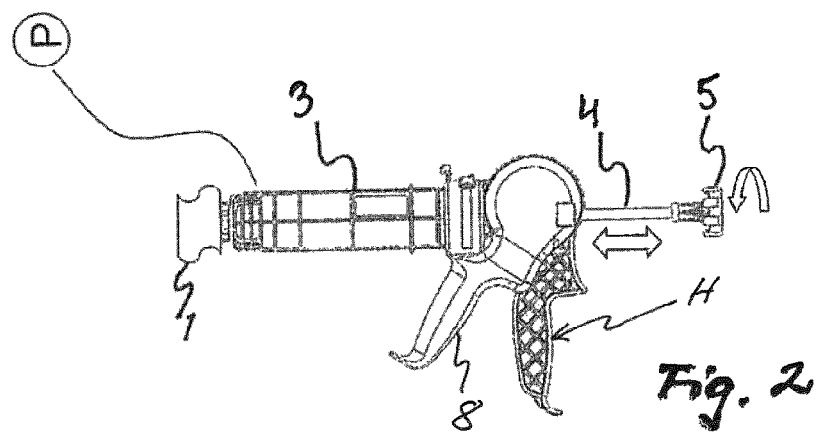

In the next step, shown in FIG. 2, the two paste components are mixed by an axially displaceable (pushed and pulled) mixing/dispensing member 4 in the cylinder 3. The mixing member 4 has mixing means 16 (FIGS. 5-11) at its end located inside the cylinder 3. After the mixing, the mixing means 16 of the mixing member 4 is connected—by a rotating movement of a knob 5—to a piston 6 (FIG. 11) of the assembly, so that these two members 6, 16 can be pushed by the mixing member 4 as a unit when dispensing the paste.

Figure 3:
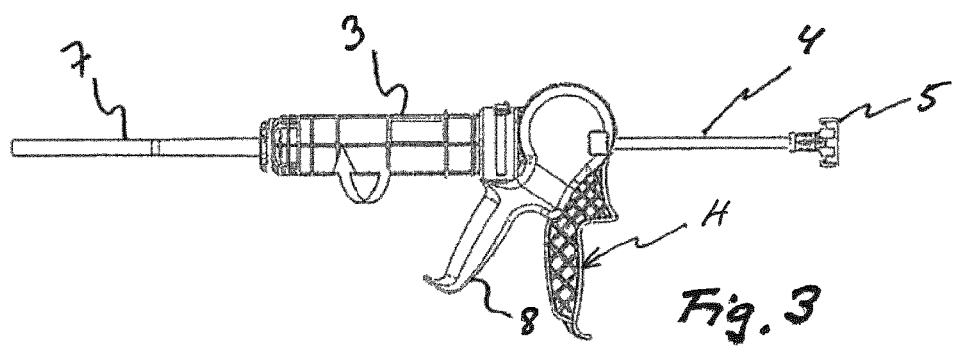
Figure 4:
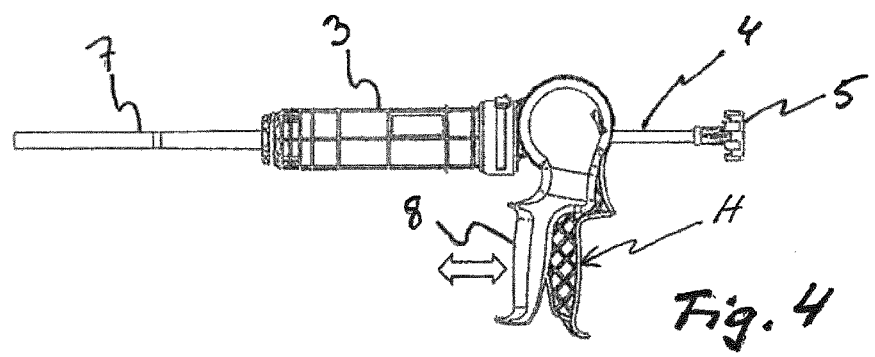

In a final step, illustrated in FIGS. 3 and 4, the receptacle 1 is removed from the connecting portion 2 and replaced by a dispensing tube 7. By moving a trigger part 8 back and forth, the piston 6 is pressed against the paste and the paste is pressed through the cylinder 3 and out of the dispensing tube 7 to the surgical area.

In the assembly shown in FIG. 5, the receptacle 1 comprises an adaptor 9 which is to be threaded into the connecting portion 2 of the cylinder 3. In an alternative embodiment, an opening device 10 is arranged inside the adaptor 9 with a portion of the receptacle 1 placed as a membrane or wall 11 over the opening device 10 (FIGS. 6 and 6a). In the embodiment shown in FIGS. 5-9, the opening device is a piercing element 10 which is coaxially aligned with the mixing member 4 in the cylinder 3, so that the central axes of the piercing element 10 and mixing member 4, respectively, coincide in the cylinder 3.

As illustrated in FIGS. 7 and 7a, a vacuum source P may be connected to the cylinder 3 at a connection 33, whereby the liquid will be sucked or pressed from the receptacle 1 into the cylinder 3 after the wall portion 11 has been pierced or perforated and thereby opened by the piercing element 10. The piercing is achieved by pushing the mixing member 4 against the piercing element 10, resulting in a movement of the piercing element 10 in a direction towards the receptacle 1 (FIGS. 7 and 7a).

Figure 12:
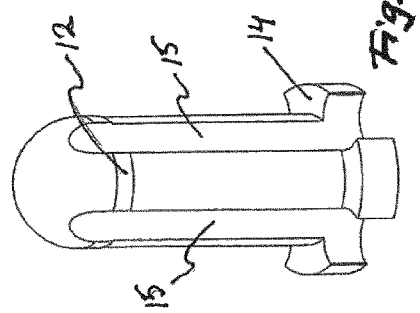
FIG. 12 is a perspective view of a piercing element according to an embodiment of the invention.
Figure 16:
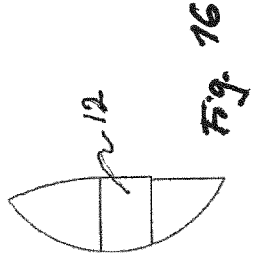
FIG. 16 shows on a larger scale a detail A of FIG. 13.
Figure 15:
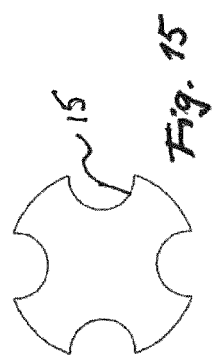
FIG. 15 is a bottom view of the piercing element.
Figure 13:
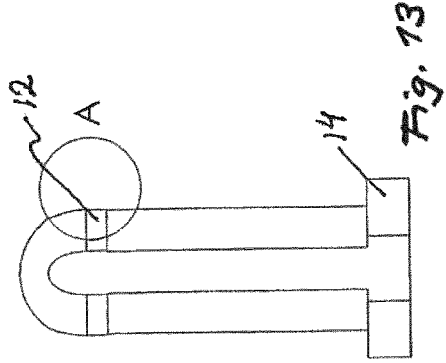
FIG. 13 is an axial cross section of the piercing element of FIG. 12.

Piercing of the receptacle 1 is achieved through the axial movement of the piercing element 10, and in one embodiment the piercing or perforating element 10 is provided with a horizontal groove 12 at its upper end (FIGS. 12, 13, 16) allowing the piercing element 10 to move only in a forward direction in the adaptor 9. The part 13 of the adaptor 9 will lock the piercing element 10 in a steady position (FIGS. 8 and 8a), and this position is also achieved by means of shoulders 14 at the end of the piercing element 10 (FIGS. 12-13, 15). The shoulders 14 prevents the piercing element 10 from leaving the adaptor 9, when pushed in a forward direction during the piercing of the wall portion 11.

Figure 14:
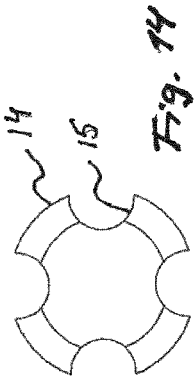
FIG. 14 is a top view of the piercing element of FIG. 12 with four longitudinal grooves.

The piercing element 10 is provided with 4 axial grooves 15 which are equidistantly distributed around the central axis of the piercing element 10 (FIGS. 12, 14, 15). After piercing of the wall portion 11 of the receptacle 1 by the piercing element 10, the liquid is sucked and pressed through the grooves 15 and into the powder containing cylinder 3 (FIGS. 9 and 9a). In the next step, liquid and powder are mixed by the operator by means of the mixing member 4 and its front mixing means 16.

After mixing of the paste, the adaptor/receptacle unit 1, 9 is removed from the cylinder 3 (FIG. 10) and replaced by the dispensing tube 7 which preferably is threadingly connected to the cylinder 3 (FIG. 11). In one embodiment, the mixing member 4 is a piston rod, whereby the mixing means 16 of the piston rod has coupling means for engagement with matching coupling means of piston 6. Thereby, the piston rod and the piston 6 can be interconnected and ready for dispensing the paste onto the surgical area, through the dispensing tube 7.

A mixing/dispensing assembly D' in accordance with a second embodiment of the invention is illustrated in FIGS. 17-27. This pre-loaded mixing gun assembly is of the same basic structure as the assembly of FIGS. 1-16, but the designs of the receptacle and the opening/piercing device differ, as will be further described below. Same or corresponding components have the same reference numerals in FIGS. 17-27 as in FIGS. 1-16, but with a (') added.

In this embodiment, the receptacle 20 is contained in a dome-shaped base unit 21 which is connectable to the connecting end portion 2' of the cylinder 3'. The collapsible receptacle 20, which contains the liquid component, is placed in a concave recess of the base unit 21 which preferably consists of a hard plastics material. The receptacle 20, which preferably is made of a flexible plastics material, has a connecting portion 22 which extends through a central opening (not shown) of the base unit 21 and which can be connected to the connection end portion 2' of the cylinder 3'. The connection portion 22, which preferably is made of a hard plastics material, has external threads for engagement with matching internal threads (not shown) in the connection end portion 2'.

Figure 25:
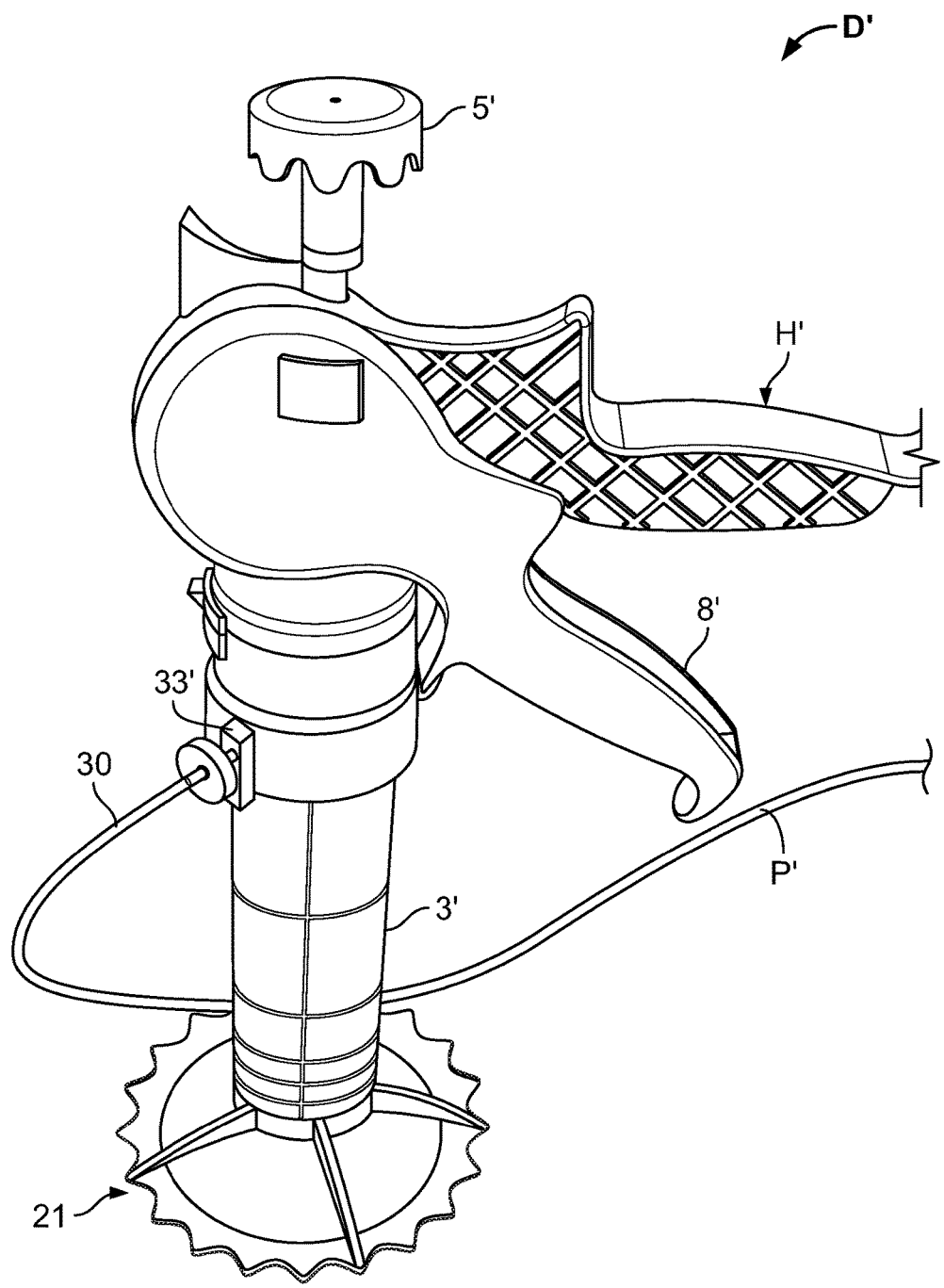
FIG. 25 shows in the perspective the assembly of FIGS. 17-20.
Figure 26:
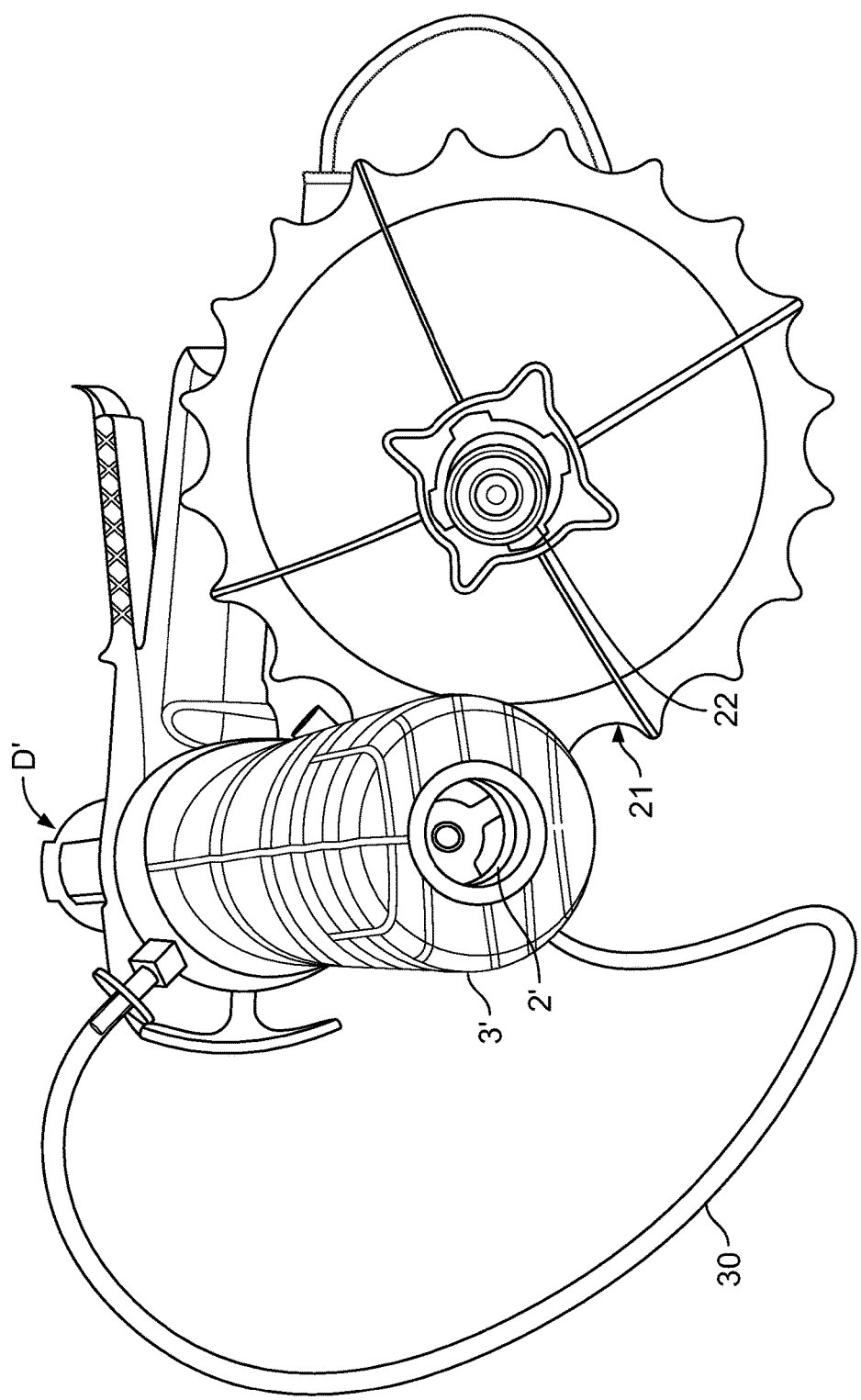
FIG. 26 shows a cylinder and a receptacle of the assembly of FIGS. 17-20.
Figure 27:
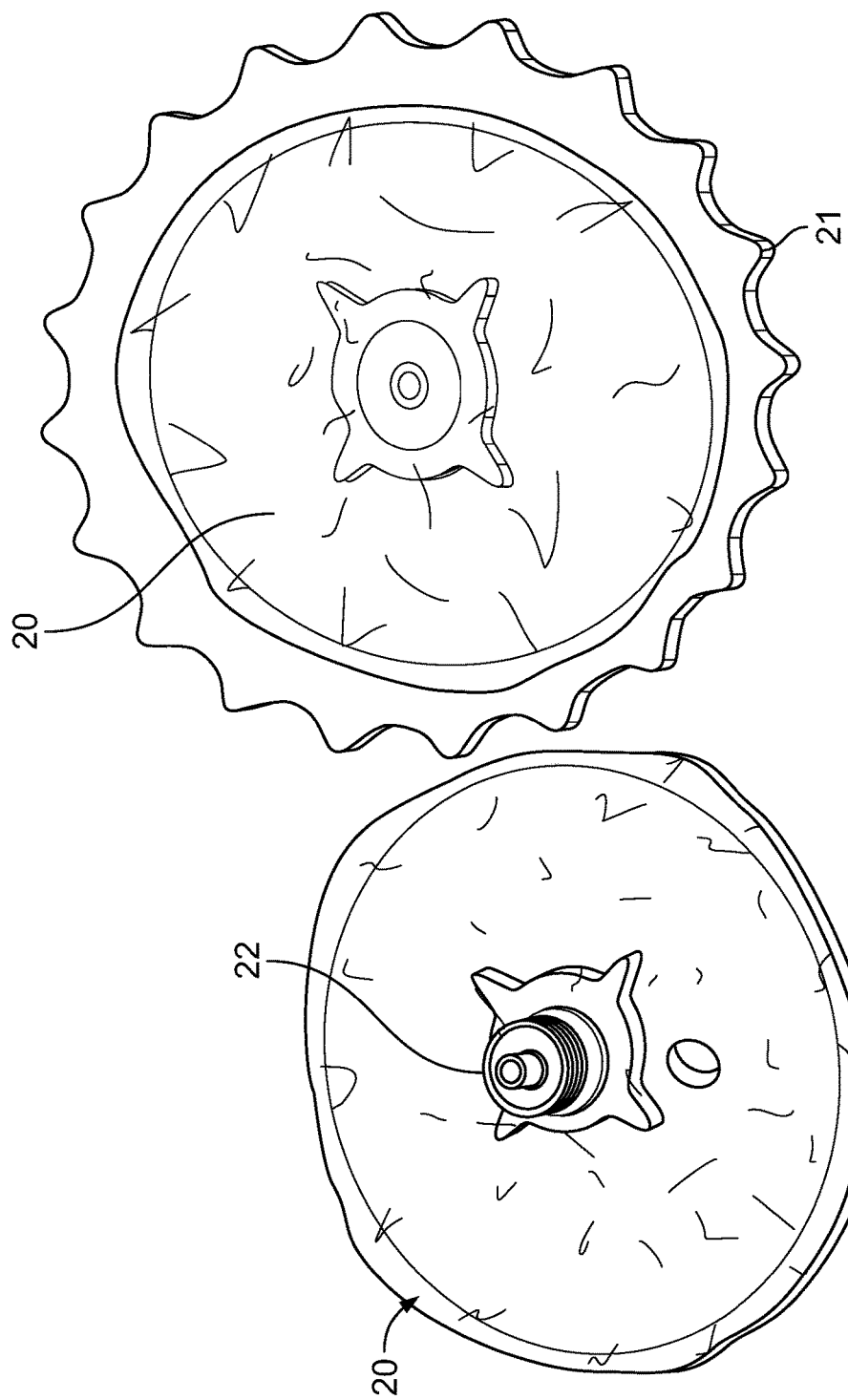
FIG. 27 shows a separate receptacle and a base unit containing a receptacle.

As can be seen in FIGS. 25-27, the dome-shaped base unit 21 has a teeth-like periphery portion which facilitates the attachment (by screwing) of the base unit 21 to the cylinder 3'; see arrow in FIG. 17. The peripheral portion of the base unit 21 also has an annular flat surface, by which it can be placed on a flat surface (see FIG. 25).

The general operation of the assembly D' will be described in the following with reference to FIGS. 17-20.

In a first step shown in FIG. 17, the base unit 21 accommodating the receptacle 20 pre-filled with the liquid component is tightened to the cylinder 3' which is pre-filled with the powder component. At the same time, a vacuum source P' is connected to the cylinder 3' at a connection 33'.

Figure 18:
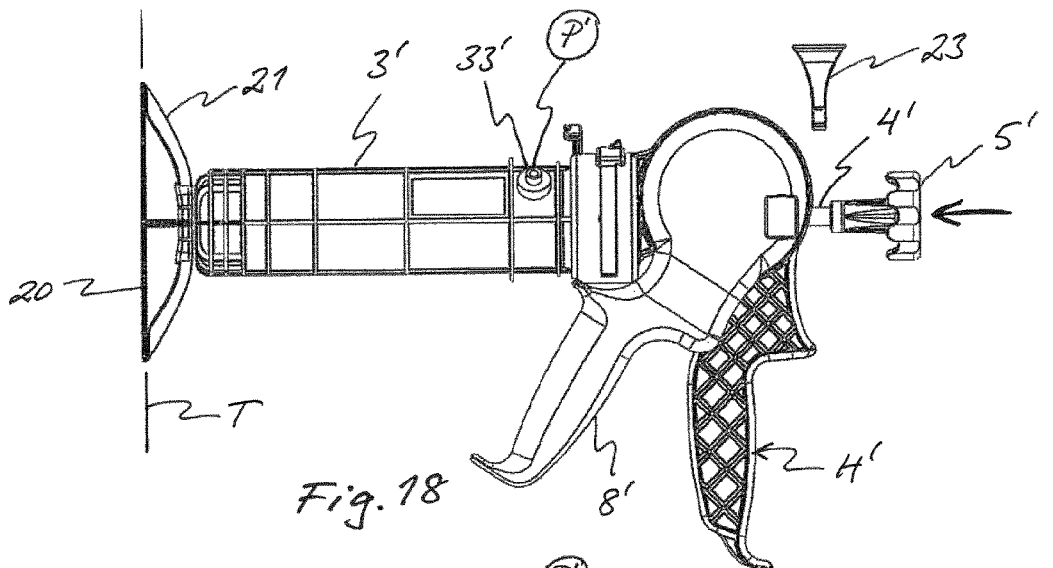
FIG. 18 shows the assembly of FIG. 17 in an activation mode.

In a second step shown in FIG. 18, the assembly D' is placed with the base unit 21 abutting against a flat surface, for instance a table T as illustrated in FIG. 25. A security lock 23 locking the mixing member 4' is removed and the piston rod 4' can be moved axially by means of the knob 5' as is illustrated by an arrow in FIG. 18.

Figure 19:
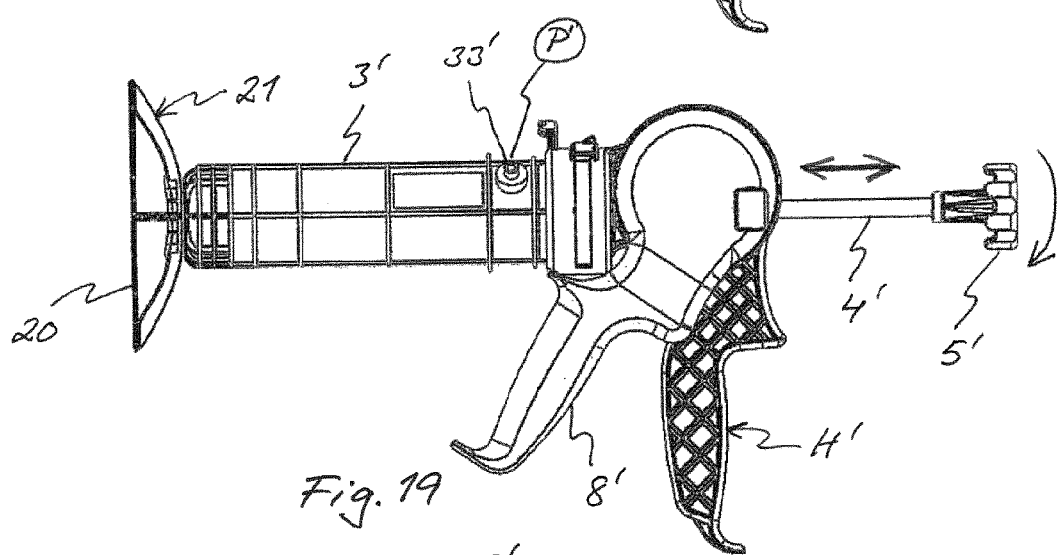
FIG. 19 shows the assembly of FIG. 17 in a mixing mode.

In a third step shown in FIG. 19, the vacuum source P' is activated and the piston rod 4' is moved axially and also turned in order to mix the powder and liquid components in the cylinder 3'. At the initial stage of this mixing mode, the free end of the mixing means 16' in the cylinder 3' is pushed against an opening or piercing device 24 which is accommodated in the connection portion 22 of the receptacle 20 (see FIG. 21-23). The opening/piercing device or element 24 breaks a wall portion or membrane of the receptacle 20 so that the liquid component can flow into the cylinder 3' and be mixed with the powder component. The vacuum created in the cylinder 3' assists the flow of the liquid into the cylinder 3'.

Figure 20:
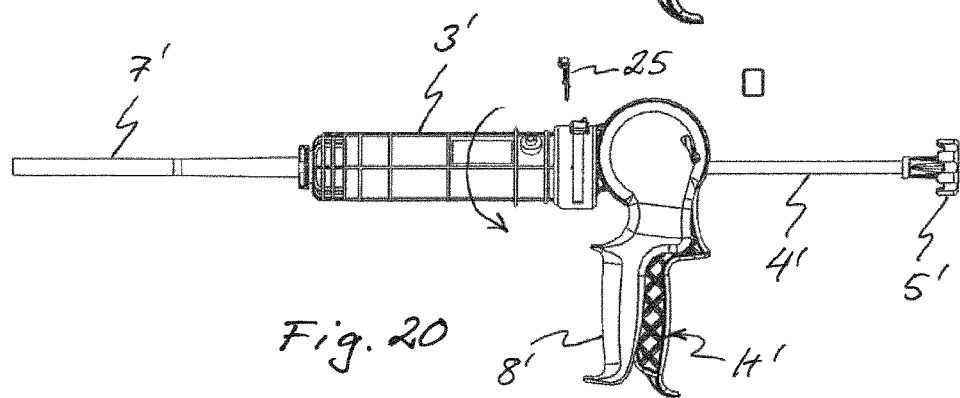
FIG. 20 shows the assembly of FIG. 17 in a dispensing mode.

In a fourth step shown in FIG. 20, following the mixing step, the base unit 21 with the empty receptacle 20 is removed from the cylinder 3' and a dispensing tube 7' is connected to the cylinder 3' at the connection end portion 2'. Hence, the dispensing tube 7' is connected to the same connection end portion 2' as is used for connection of the base unit 21. The vacuum source P' is disconnected and a further security lock 25 is removed from the assembly D'. By turning the cylinder 3' as is shown by an arrow in FIG. 20, the assembly D' is put in dispensing mode in which the mixing means 16' is connected to the piston 6' so that the mixed paste can be dispensed from the cylinder 3' via the dispensing tube 7' (see FIG. 24).

In the following, the operation of the opening/piercing device 24 will be described in more detail with reference to FIGS. 21-23.

Figure 21:
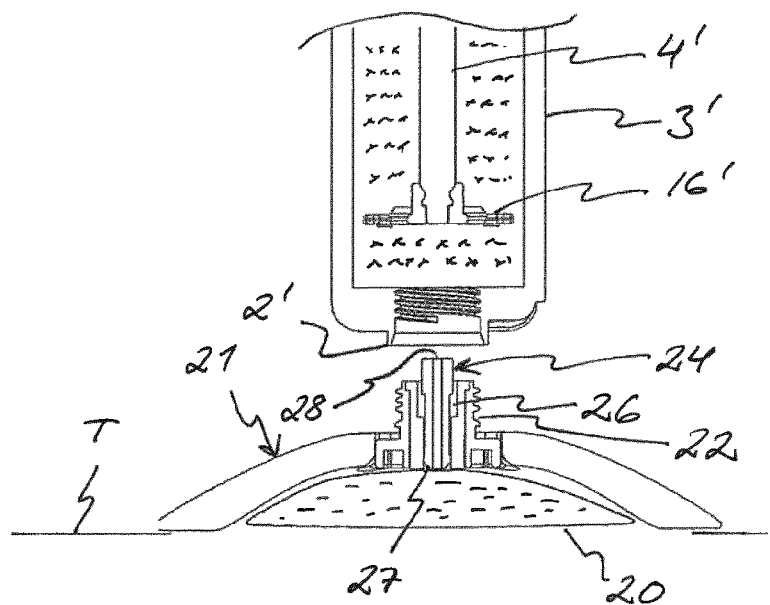
FIG. 21 shows—on a larger scale—the preparation mode.

In FIG. 21, which corresponds to the mode shown in FIG. 17, the piercing device 24 received in the connection portion 22 of the receptacle 20 is in its inactive position. The piercing device 24 is axially moveable in an axial bore 26 of the connection portion 22. In the pre-emptying mode of the receptacle 20, the tip 27 of the piercing device 24 is in abutment against the wall or membrane of the receptacle 20, as is shown in FIG. 21. The piercing device 24 has an internal axial bore or channel 28 for flow of liquid.

Figure 22:
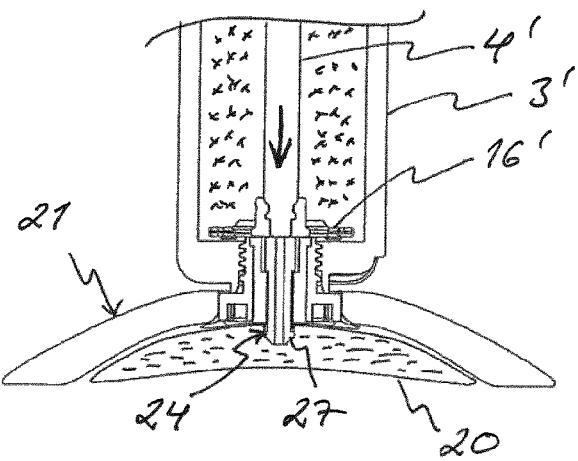
FIG. 22 shows—on a larger scale—the activation mode.

In FIG. 22, which corresponds to the mode shown in FIG. 18, the mixing means 16' has pushed the piercing device 24 axially in the bore 26 so that the tip 27 has pierced or perforated the wall portion or membrane of the collapsible receptacle 20 (see arrow). After this piercing, the liquid contained in the receptacle 20 flows into the cylinder 3' through the flow channel 28. The liquid flowing into the cylinder 3' is mixed with the powder contained therein and the bone cement paste is gradually created by this mixture.

Figure 23:
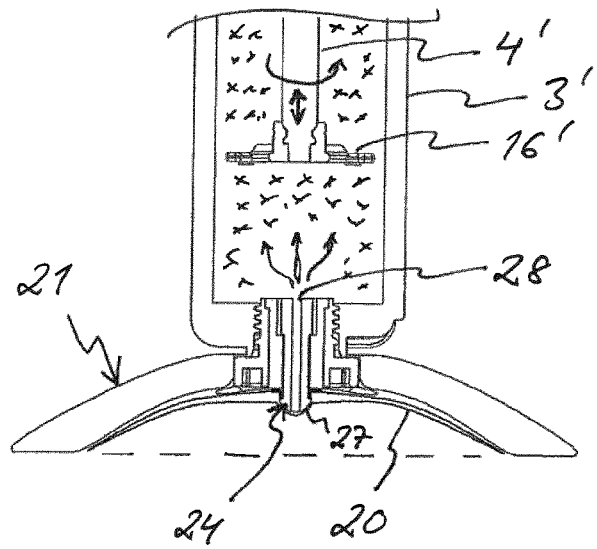
FIG. 23 shows—on a larger scale—the mixing mode.
Figure 24:
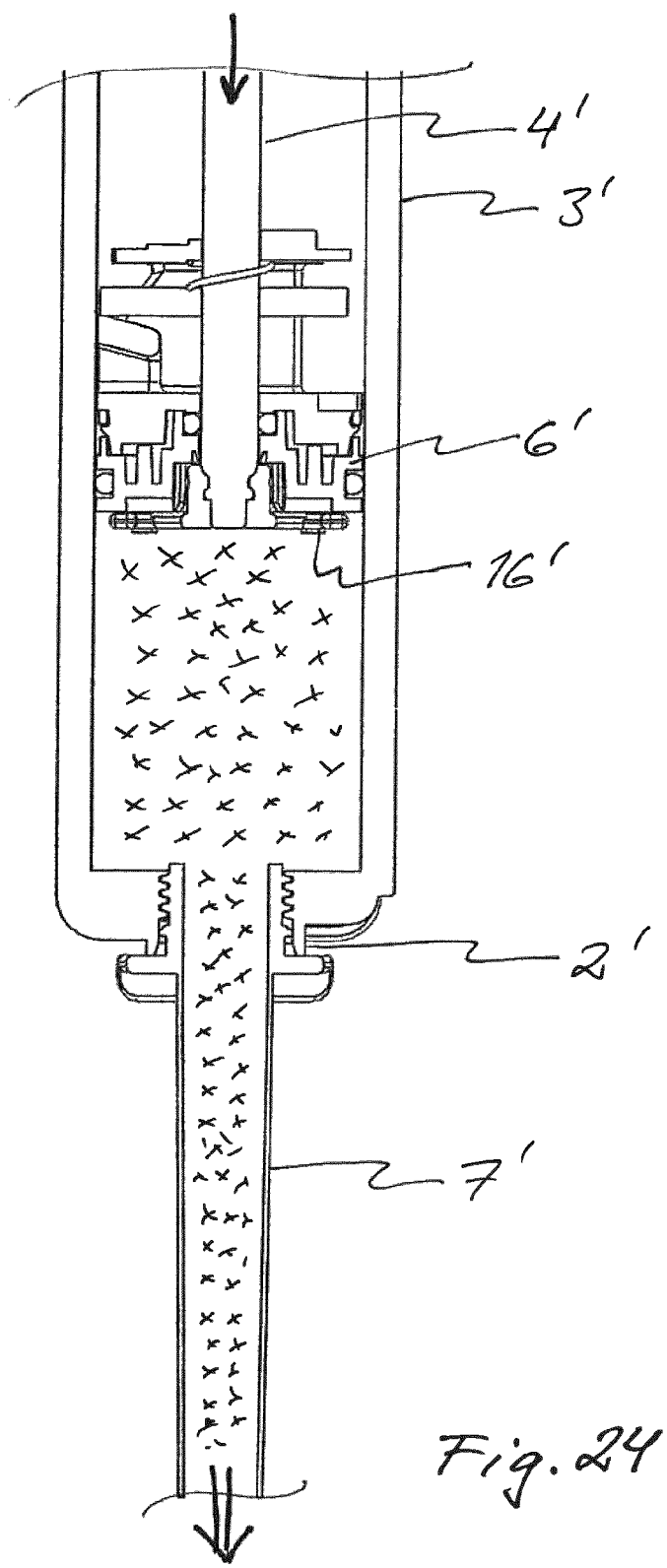
FIG. 24 shows—on a larger scale—the dispensing mode.

In FIG. 23, which corresponds to FIG. 19, the receptacle 20 is emptied and has collapsed into the concave cavity of the base unit 21. The mixing means 16' is now axially reciprocated within the cylinder 3' and also turned as is shown by arrows in FIG. 23. Hereby, the liquid fed into the cylinder 3' is thoroughly mixed with the powder therein and the desired bone cement paste is completed and ready to be dispensed. In this mode, the piercing or perforating device 24 is maintained in its piercing/perforating position in the connection portion 22.

When the mixing of the paste is completed, the base unit 21 with the empty receptacle 20 is removed from the cylinder 3' and the dispensing tube 7' is connected to the cylinder 3' at the same connection end. The mixing means 16' is engaged with and connected to the piston 6' which can be pushed in the direction of the arrow in FIG. 24 so that the mixed paste can be dispensed out of the dispensing tube 7'.

The assembly D' is shown in its preparation mode in FIG. 25, in which the base unit 21 is placed on a table T. A conduit 30 is connected at 33' to the cylinder 3' and is in communication with the vacuum source P'. The positioning of the pre-loaded mixing gun D' vertically with the connected base cup unit 21 placed on the table T is favourable since the user can easily operate the assembly by pushing and turning the knob 5' for mixing the liquid and powder within the cylinder 3'. The base unit 21 provides a very stable position for the mixing gun. Furthermore, it is easy for the user to handle the vacuum source connection in this mode.

FIG. 26 shows the connection end portion 2' of the cylinder 3' which is to be connected to the connection portion 22 of the receptacle 20 accommodated in the base unit 21. Preferably, the cylinder 3' is pre-filled with the powder and the receptacle 20 is pre-filled with the liquid. Along with the dispensing tube 7', these two components 3' and 20/21 form a kit which constitutes a pre-loaded assembly to be used for instance in hip joint replacement surgery and the like.

To the left in FIG. 27 a transparent flexible receptacle 20 is shown separately, and to the right there is shown a base unit 21 with an empty collapsed receptacle 20. The member made up by the receptacle 20 and the base unit 21 is very easy to handle by users, and it can be stored in an efficient manner.

It is appreciated that the inventive concept is by no means limited to the embodiments described herein, and modifications are feasible within any derivation from the inventive idea set forth in the appended claims. Although vacuum is used in the embodiments described as examples, it should be appreciated that the flow of liquid from the flexible receptacle into the cylinder can be accomplished in other ways. Liquid can also be fed into the cylinder by applying an external force or pressure on the flexible receptacle to that liquid is pushed into the cylinder. Feeding of liquid into the cylinder can also be achieved by applying an overpressure to the flexible container. As long as there is a suitable differential pressure between the receptacle and the cylinder, which aims at forcing or drawing the liquid into the cylinder, the aimed at function of the mixing gun assembly will be achieved.

The invention claimed is:

1. An assembly for preparing and dispensing a paste, comprising:
    a cylinder for mixing a powder component and a liquid component forming the paste, and a receptacle containing the liquid component, said receptacle being connectable to the cylinder;

said cylinder comprising a dispensing end portion to which a dispensing tube for dispensing mixed paste is connectable, a mixing member for mixing the powder and liquid components in the cylinder and for pressing the paste through the dispensing tube and to a designated area, and a connecting portion for connecting the receptacle to the cylinder;

said connecting portion for connecting the receptacle to the cylinder being provided at the dispensing end portion of the cylinder in such a way that the receptacle is connectable to said dispensing end portion;

said assembly further comprising an opening device configured to open the receptacle in order to allow the liquid component to flow out of the receptacle and into the cylinder by means of a differential pressure between the cylinder and the receptacle, for mixing with the powder component contained in the cylinder;

said opening device being operated by said mixing member for opening the receptacle;

said receptacle being at least partially collapsible for allowing said flow of the liquid component into the cylinder by said differential pressure; and said assembly being a single-use assembly or a pre-loaded assembly.

2. The assembly as claimed in claim 1, wherein the opening device is provided on the cylinder or on a member connected to the same.

3. The assembly as claimed in claim 1, wherein the opening device is provided on the mixing member.

4. The assembly as claimed in claim 1, wherein the opening device is provided on the receptacle or on an adaptor/connection portion which is provided on the receptacle and configured to connect the same to the cylinder.

5. The assembly as claimed in claim 4, wherein the opening device is arranged movable in said adaptor/connection portion of the receptacle and operable by the mixing member.

6. The assembly as claimed in claim 1, wherein said mixing member comprises a piston rod.

7. The assembly according to claim 6, wherein said piston rod is displaceable and rotatable in a piston having an element for mixing the paste ingredients in the cylinder; wherein locking means being configured to lock the piston in any position along the piston rod; and interconnecting means being configured to interconnect the piston and the piston rod to allow displacement of the piston in the cylinder by means of the piston rod for dispensing of the mixed paste outside the cylinder.

8. The assembly as claimed in claim 1, wherein the opening device comprises an elongate piercing element which is displaceable, and which is configured to pierce a wall portion of the receptacle so that the liquid component is allowed to flow out of the receptacle and into the cylinder by means of said differential pressure.

9. The assembly as claimed in claim 8, wherein the piercing element is displaceable in an axial direction coaxial with the center axis of the cylinder.

10. The assembly as claimed in claim 8, wherein the piercing element has a cylindrical shape and a piercing end which is rounded.

11. The assembly as claimed in claim 8, wherein the piercing element comprises a bottom portion which in use is directed towards the cylinder and which is configured to prevent said piercing element from leaving the cylinder when pressed by the mixing member.

12. The assembly as claimed in claim 8, wherein the piercing element at its piercing end comprises a circumferential groove which extends around said piercing element and which allows the piercing element to move only in a direction towards the receptacle.

13. The assembly as claimed in claim 8, wherein the piercing element comprises external, axial grooves which are configured to—after said piercing—allow the liquid component to flow from the receptacle to the cylinder.

14. The assembly as claimed in claim 13, wherein said external, axial grooves are provided equidistantly on the external surface of the piercing element with respect to the center axis thereof.

15. The assembly as claimed in claim 8, wherein the piercing element comprises a central liquid flow channel.

16. The assembly as claimed in claim 1, wherein the receptacle is accommodated in a base unit.

17. The assembly as claimed in claim 16, wherein the base unit including the receptacle is connectable as one member to said connection end portion of the cylinder.

18. The assembly as claimed in claim 16, wherein the base unit is dome shaped and comprises a peripheral portion which has an annular flat surface.

19. The assembly as claimed in claim 18, wherein the base unit has external teeth along its peripheral portion.

20. A method of preparing a paste, by means of an assembly as claimed in claim 1, comprising the steps of:
  connecting the liquid containing receptacle to the powder containing cylinder at the dispensing end portion of the cylinder;
  creating a differential pressure between the cylinder and the receptacle;
  activating the opening device by means of the mixing member so that the receptacle is opened and the liquid component—by said differential pressure—is drawn from the receptacle into the cylinder where it is mixed with the powder component to form said paste, said receptacle collapsing at least partially when being emptied.

21. The method as claimed in claim 20, wherein said opening of the receptacle comprises piercing a wall portion of the receptacle so that the liquid component flows out of the receptacle and into the cylinder by means of said differential pressure.

22. The method as claimed in claim 21, wherein said piercing is achieved by the mixing member pushing on a moveable piercing element.

23. The method as claimed in claim 20, wherein the liquid and powder component are mixed in the cylinder by reciprocal movement of the mixing member in the cylinder after said opening of the receptacle.

24. A kit for preparing a paste, comprising:
  a cylinder pre-filled with a powder component, a receptacle pre-filled with a liquid component and a dispensing tube as defined in claim 1.

25. The assembly according to claim 1, for preparing and dispensing a paste comprising the cylinder being pre-filled with the powder component.

26. The assembly according to claim 1, wherein the paste comprises bone cement.

27. The assembly as claimed in claim 8, wherein said differential pressure comprises a vacuum in said cylinder.

28. The assembly as claimed in claim 10, wherein the cylindrical shape and the piercing end is semi-spherical.

29. The method of preparing a paste according to claim 20, wherein the paste comprises bone cement.

30. The method as claimed in claim 21, wherein said differential pressure comprises a vacuum in said cylinder.

31. The kit according to claim 24, wherein the paste comprises bone cement.

32. The kit according to claim 24, further comprising means for connecting the cylinder to a vacuum source.

\* \* \* \* \*